United States Patent [19]

Sako et al.

[11] Patent Number: 4,532,211
[45] Date of Patent: Jul. 30, 1985

[54] COLIFORM BACILLUS HAVING A GENE FOR THE PRODUCTION OF STAPHYLOKINASE AND A PROCESS FOR PRODUCTION OF STAPHYLOKINASE THEREWITH

[75] Inventors: Tomoyuki Sako; Saeko Sawaki; Toshizo Sakurai; Masahiko Mutai; Isamu Kondo, all of Tokyo, Japan

[73] Assignee: Kabushiki Kaisha Yakult Honsha, Tokyo, Japan

[21] Appl. No.: 434,503

[22] Filed: Oct. 15, 1982

[30] Foreign Application Priority Data

Oct. 16, 1981 [JP] Japan ................................. 56-164064

[51] Int. Cl.³ ...................... C12P 21/00; C12P 21/02; C12P 21/04; C12N 9/48; C12N 9/50; C12N 1/20; C12N 1/00; C12N 15/00; C07H 21/04
[52] U.S. Cl. .................................. 435/172.3; 435/68; 435/70; 435/71; 435/212; 435/219; 435/220; 435/253; 435/317; 536/27; 935/14; 935/29; 935/73; 935/82
[58] Field of Search ...................... 435/68, 70, 91, 172, 435/253, 317, 71, 212, 219, 220, 172.3; 536/27

[56] References Cited

U.S. PATENT DOCUMENTS 4,366,246 12/1982 Riggs .................................... 435/68

OTHER PUBLICATIONS

Blair et al., "Phage Typing of Staphylococci", pp. 771–784, (1961), Bull. World Health Org.
Mason et al., "Can. J. Microbiol." vol. 21, pp. 1113–1116, (1975).
Kondo et al., "Infection and Immunity", vol. 18, No. 2, pp. 266–272, (1977).
Kondo et al., "Staphylococcal Phages Mediating the Lysogenic Conversion of Staphylokinase", pp. 357–362, (1981).
Cohen et al., "Proc. Nat. Acad. Sci", vol. 70, No. 11, pp. 3240–3244, (1973).
Chang et al., "Proc. Nat. Acad. Sci.", vol. 71, No. 4, pp. 1030–1034, (1974).
Bolivar et al., "Construction and Characterization of New Cloning Vehicles", pp. 95–113, (1977).
Talmadge et al., "Proc. Natl. Acad. Sci.", vol. 77, No. 6, pp. 3369–3373, (1980).
Löfdahl et al: J. Virol. 37, 795, (1981).
Sako et al: Mol Gen. Genet. 190, 271, (1983).
Kondo et al: In: Jeljaszewicz (ed), *Staphylococci and Staphylococcal Infections,* Gustav Fisher Verlag, New York, p. 357, (1981).

*Primary Examiner*—Thomas G. Wiseman
*Assistant Examiner*—James Martinell
*Attorney, Agent, or Firm*—Birch, Stewart, Kolasch & Birch

[57] ABSTRACT

Novel coliform bacillus useful for industrial production of staphylokinase, a fibrinolytic enzyme, and process for the production of staphylokinase using said microbe are provided. The novel microbe comprises a recombinant DNA, carrying genetic information for the production of staphylokinase, said genetic information being DNA derived from a temperate phage DNA of *Staphylococcus aureus.*

33 Claims, No Drawings

COLIFORM BACILLUS HAVING A GENE FOR THE PRODUCTION OF STAPHYLOKINASE AND A PROCESS FOR PRODUCTION OF STAPHYLOKINASE THEREWITH

BACKGROUND OF THE INVENTION (1) Field of the Invention

This invention relates to a novel coliform bacillus, *Escherichia coli* (hereinafter referred to as *E. coli*), having a gene for staphylokinase production (hereinafter referred to as "SAK gene") and to a process for the production of staphylokinase by use of the novel microbe.

(2) Description of the Prior Art

Staphylokinase (hereinafter referred to as SAK) is a fibrinolytic enzyme which is produced by *Staphylococcus aureus* (hereinafter referred to as *S. aureus*).

The function of SAK is to transform plasminogen in blood into plasmin, which in turn acts on fibrin to lyse the same. There are known, as enzymes of similar activity, urokinase which is present in human urine and streptokinase which is produced by streptococci. All these enzymes find use in medicine as fibrinolytics, for example, anticoagulants (blood coagulation inhibitors) and antithrombotics. In view of such usefulness, many attempts have been made to improve processes for the production, extraction and purification of these enzymes.

It is known that capability for producing SAK is a trait imparted to a *S. aureus* host by way of what is called lysogenic conversion, i.e., lysogenization of the host with a temperate phage. Accordingly, prior art processes for the production of SAK comprise selecting from strains of *S. aureus* a strain having SAK producibility, or lysogenizing a *S. aureus* strain incapable of SAK production with a phage capable of lysogenic conversion of SAK, culturing, in either case, the obtained strain and obtaining SAK from the culture.

*S. aureus* is, however, a pathogenic bacterium and so cautious consideration is required in the handling thereof. Therefore, prior art processes are not particularly suited for SAK production on an industrial scale. Moreover, in order to achieve high yields of SAK, it is necessary to carry out cultivation for a long period of time. In this regard, also, the prior art processes have drawbacks for SAK production on an industrial scale.

SUMMARY OF THE INVENTION

Extensive research has been conducted for a process which is suitable, from the standpoint of both safety and efficiency, for SAK production on an industrial scale. As a result, it has been discovered that the gene coding for SAK production is located on phage DNAs and a SAK gene-carrying fragment of a temperate phage of *S. aureus* has successfully been introduced, through a vector, into *E. coli*.

Thus, according to the present invention, there is provided novel coliform bacillus *E. coli*, having a SAK gene as well as a process for the production of SAK wherein the novel microbe is cultured.

DETAILED DESCRIPTION OF THE INVENTION

The novel microbe, *E. coli*, according to the present invention can be prepared by the following steps (1) through (6):

(1) digesting a temperate phage DNA of *S. aureus* as a DNA donor with one or more restriction enzymes;

(2) optionally isolating the digested DNA fragment carrying genetic information for SAK production (this step may be skipped);

(3) cleaving a vector DNA with one or more restriction enzymes;

(4) inserting the fragment obtained in Step (1) or (2) into the cleaved site of the vector DNA obtained in step (3) to obtain recombinant DNA having SAK gene;

(5) introducing of the thus obtained recombinant DNA into an *E. coli* host; and (6) selectively separating transformed E. coli cells which possess the capability of producing SAK as a result of the operation in Step (5).

As the DNA donor, in the above Step (1), any strain of phage may be employed which is separated from a lysogenic strain of *S. aureus* and which is capable of lysogenic conversion. Examples of such phage strains include 42D, L42E and 77 (Mason, R. E. and Allen, W. E. (1975) Can. J. Microbiol. 21, 1113–1116); P$\phi$1, P$\phi$2, T$\phi$–42D and P$\phi$–406 (Kondo, I. and Fujise, K. (1977) Infect. Immun. 18, 266–272); R$\phi$19 and S$\phi$C (Kondo, I. et al (1980) Tokyo Jikei-kai Ika-Daigaku Zasshi 95, 1203–1206).

Preparation of temperate phage DNAs may be carried out by conventional methods in the art, which comprise infection a strain of *S. aureus* as the host with a temperate phage strain and culturing the thus infected microbe (see, for example, Blair, J. E. and Williams, R. E. O. (1961) Bull. W. H. O. 24, 771–784). As a result of the cultivation, the cells are lysed and the phage is released into the culture medium. The thus released phage is collected by an appropriate method (for example by CsCl equilibrium density gradient centrifugation as described in Rosenblum, E. D. and Tyrone, S. (1964) J. Bacteriol. 88, 1737–1742). Isolation of the phage DNA from the thus collected phage may be carried out by methods known per se in the art, for example, by extraction with phenol.

Digestion of temperate phage DNAs with one or more restriction enzymes may be carried out in the following manner.

An appropriate restriction enzyme is added to the phage DNA and brought into reaction therewith under appropriate conditions, with the result that the phage DNA is digested into fragments which vary with the restriction enzyme used.

Restriction enzymes suitable for digesting the phage DNA are required (1) to be able to excise the phage DNA and (2) not to excise the DNA region carrying genetic information for SAK production. Preferred examples of such restriction enzymes include HindIII, PstI, AccI, AvaII, EcoRI, HpaI, HpaII, HindII, SstI, ClaI, BstEII, SstII, XhoI, BclI, BglII, PvuII, XorII, KpnI, SmaI and XbaI.

After digestion, the DNA fragment carrying genetic information for SAK production is isolated from the restriction fragments of the phage DNA. The isolation may be carried out by means known per se in the art, for example by agarose gel electrophoresis. In carrying out the isolation, it is necessary to determine beforehand which one of the restriction fragments from the phage DNA carries genetic information for production of SAK. Regarding the method for the above determination, further detailed discussion will be made hereinbelow. As mentioned hereinabove, this isolation step may be skipped if desired or necessary.

Cleavage of vector DNAs can be carried out by adding an appropriate restriction enzyme to the vector DNA and bringing them into reaction under appropriate conditions.

For the purpose of the present invention any vector DNA known in the art may be used. Preferred examples of vector DNAs include ColEI, pMB9, pSC101 and p15A and their derivatives such as pBR322 and pACYC184, as well as Charon vectors derived from λ phage.

Insertion of the above said DNA fragment carrying the SAK gene into the vector DNA at the site of cleavage of the latter can be carried out by conventional means. Suitable reaction conditions will be chosen dependent upon the kinds of the phage DNA, vector DNA and restriction enzyme used.

Insertion of the phage DNA fragment carrying the SAK gene into the vector DNA may take place in any orientation and at any site as long as the vector's capability for replication is not impaired.

In the next step (Step (5)), the resultant recombinant DNA is introduced into an E. coli host. As the E. coli host, all E. coli strains are usable whose restriction-modification system is devoid of restriction capability. When E. coli having restriction capability is used as the E. coli host, the recombinant DNA which is to be introduced should have already been modified by any modification system which can be either in vitro or in vivo. The type of the E. coli host may be limited dependent upon the kind of the vector used. In the designation of the E. coli strains used, "$r_K{}^-$" represents a strain which is devoid of restriction capability and "$m_K{}^-$" represents a strain which is devoid of modification capability and "$m_K{}^=$" represents a strain having modification capability.

The introduction of the recombinant DNA can be carried out by means and techniques known per se, as described, for example, in Cameron et al. (1975) Proc. Natl. Acad. Sci., U.S.A. 72, 3416–3420.

Even when Step (2) is carried out, it sometimes happens that no insertion of the SAK gene-carrying DNA fragment of lysogenic phages takes place. Furthermore, when Step (2) is skipped, there is a possibility, in addition to the above-mentioned possibility of no insertion taking place, that other DNA fragments not relevant to SAK production are inserted. In order to overcome these problems it is necessary to make selective separation of E. coli cells which have gained capability for producing SAK. For this purpose it is convenient to employ the procedure known to be used for S. aureus, as described in Kondo, I. and Fujise, K. (1977) Infect. Immun. 18, 266–272. Thus, in accordance with the known procedure, heated plasms agar medium is prepared and the microbes to be tested are spotted thereupon and grown for a given period of time to examine the fibrinolytic activity. Transparent lytic halos form around colonies of microbes having fibrinolysis ability. The desired SAK-producing E. coli can be isolated from these colonies. Analysis of the SAK gene-carrying DNA from the SAK-producing E. coli can be carried out in the following manner. The recombinant plasmid or the recombinant phage is separated from the SAK-producing E. coli and digested with the same restriction enzyme(s) as that or those used for the digestion of the phage DNA and for the cleavage of the vector DNA. The molecular weights (i.e., the DNA lengths) of the resultant DNA fragments are measured by means known in the art, for example, by agarose gel electrophoresis, whereby it is possible to locate the SAK gene-carrying DNA fragment on the phage DNA.

An example of such analysis is shown below.

Analytical Example

SφC DNA was employed as phage DNA. It was recognized to have the genetic information for production of SAK:

(1) when digested with restriction enzyme PstI, within the segment of 15.8 kb;
(2) when digested with restriction enzyme HindIII, within the segment of 4.9 kb;
(3) when digested with restriction enzymes HindIII and AvaII, within the segment of 2.0 kb; and
(4) when digested with restriction enzymes AvaII and AccI, within the segment of 1.3 kb.

The SAK-producing E. coli obtained by the foregoing process has the same microbiological characteristics as those of the original E. coli, except in that the former E. coli is capable of producing SAK. Some of the general microbiological characteristics, determined with the E. coli strains obtained in the Examples referred to later, are shown in the following Table.

TABLE

MICROBIOLOGICAL CHARACTERISTICS OF E. coli STRAINS IMPARTED WITH CAPABILITY OF PRODUCING SAK AS WELL AS E. coli HOST

|  | A* negative bacillus | B** negative bacillus | C*** negative bacillus |
|---|---|---|---|
| Gram's staining and Morphology | | | |
| Catalase production | + | + | + |
| Oxidase production | − | − | − |
| OF test | F | F | F |
| Acid production from glucose | + | + | + |
| Gas generation from glucose | + | + | + |
| Nitrate reducibility | + | + | + |
| Phenylalanine deaminase activity | − | − | − |
| Lysine decarboxylase activity | − | − | − |
| Ornithine decarboxylase activity | − | − | − |
| Urease activity | − | − | − |
| Hydrogen sulfide production | − | − | − |
| Indole production | + | + | + |
| ONPG decomposability | − | − | − |
| DNA decomposition activity | − | − | − |
| Citrate assimilability | − | − | − |
| Maronate assimilability | − | − | − |
| Acid production from saccharides | | | |
| from lactose | − | − | − |
| from arabinose | + | + | + |
| from inositol | − | − | − |
| from rhamnose | + | + | + |

*A represents E. coli K12 C600 $r_K{}^- m_K{}^-$
**B represents E. coli K12 C600 $r_K{}^- m_K{}^-$ (pSAK-HP2)
***C represents E. coli K12 C600 $r_K{}^- m_K{}^-$ (pSAK 361)

According to the present invention there is provided an industrially advantageous process for the production of SAK which comprises culturing the novel E. coli obtained in the manner described previously and collecting SAK which accumulates in the cultured cells.

The SAK production process of the present invention is carried out by culturing, in a conventional manner, the SAK-producing E. coli obtained in the manner described above, harvesting the cultured cells and then collecting the periplasmic fraction, from which most of the SAK activity substance is obtained. Collection of the periplasmic fraction can be carried out by means and techniques known per se in the art (see, for example, Talmadge, K. et al. (1980) Proc. Natl. Acad. Sci. U.S.A. 77, 3369–3373 which is hereby expressly incorporated by reference). The process of the invention is novel and effective, and different from the prior art process with *S. aureus* wherein the supernatant of the culture is collected. Thus, it is possible to recover SAK as a product from the periplasmic space for the first time by the process of the present invention, in which SAK can be produced by *E. coli*. This is one of the characteristic advantages of the process of the present invention.

Purification of the thus obtained SAK may be carried out by conventional means for purification of proteins, for example, by salting out, gel filtration or adsorption chromatography.

Thus, according to the process of the present invention, which has enabled *E. coli* to produce SAK, there are offered many outstanding advantages, over the prior art with *S. aureus*, in respects such as safety, growth rate and feasibility of mass culture (i.e., mass production). Further outstanding advantages, which all stem from the fact that SAK accumulates in the periplasmic space, are that SAK is obtained in more than one hundred times higher concentrations than in the case of the prior art with *S. aureus* in which SAK is obtained from supernatant fraction, and that the isolation and purification of SAK can be carried out in an easier manner than by the method which involves crushing of the whole cell followed by extraction, because of less content of proteinaceous contaminants.

The above-mentioned phenomenon of SAK accumulation in the periplasmic space can be demonstrated by the following example. The *E. coli* strain, *E. coli* K12 C600 $r_K^- m_K^{31}$ (pSAK 361), which was obtained in Example 1 described hereinafter was cultured at 37° C. for 5 hours in 200 ml of L broth. The SAK accumulated in the periplasm in a greater concentration than cytoplasm and the supernatant. The distribution and ratio of SAK activity is shown below.

|  | Total activity (u) | % |
| --- | --- | --- |
| Supernatant fraction | 950 | 23 |
| Periplasmic fraction | 2400 | 58 |
| Cytoplasmic fraction | 800 | 19 |

This result shows that about 60% of SAK is present in the periplasmic fraction.

The following examples serve to illustrate the present invention without limiting it.

EXAMPLE I

In this example SφC was used as the DNA donor, pBR322 as the vector DNA, HindIII as the restriction enzyme, and *E. coli* K12 C600 $r_K^- m_K^{31}$ or *E. coli* K12 WA802 $r_K^- m_K^=$ as the host *E. coli* strain.

(A) Preparation and Digestion of SφC DNA

Phage SφC was grown in accordance with the method described in Blair, J. E. and Williams, R. E. O. (1961) Bull. W. H. O. 24, 771–784. To 1 liter of the resulting phage lysate was added 100 ml of 5M-NaCl and then 300 ml of 30% (w/w) polyethylene glycol. The mixture was stirred well and allowed to stand at 0° C. for several hours. The mixture was then subjected to centrifugation at 10,000 rpm for 15 minutes to obtain the precipitate. The precipitate was dissolved in 20 ml of a buffer containing 10 mM Tris-HCl (pH 7.4), 10 mM MgSO₄, 5mM CaCl₂ and 0.01% gelatin. To the resulting solution were added DNase and RNase in a manner such that the final concentration of each enzyme became 1 μg/ml. The reaction was carried out at 37° C. for 20 minutes. After the reaction, the mixture was centrifuged at 10,000 rpm for 10 minutes and the supernatant was further centrifuged at 30,000 rpm for 60 minutes. The thus deposited precipitate was dissolved in 2.5 ml of the same buffer as described above. About 1.7 g of cesium chloride was added to the solution and the mixture was subjected to equilibrium density gradient centrifugation at 27,000 rpm for 18 hours. The thus obtained band of the phage was separated and dialyzed against 1 liter of the same buffer as described above. To 0.5 ml of the dialyzed phage suspension were added 50 μl of 1.5 M NaCl 0.15 M sodium citrate, 5 μl of 250 mM disodium salt of EDTA (pH 7.0) and 5 μl of 10% SDS. After the mixture was allowed to stand at 37° C. for 5 minutes, 0.6 ml of phenol saturated with 0.15 M NaCl - 15 mM sodium citrate solution was added thereto and the resulting mixture was gently stirred at room temperature for about 10 minutes. The mixture was then subjected to centrifugation at 3,000 rpm for 10 minutes to collect the upper phase (i.e., aqueous phase). The aqueous phase was subjected to the phenol treatment described above and then washed three times with equivolumes of ether. The resulting aqueous phase was dialyzed three times against 200 ml of 0.15 M NaCl—15 mM sodium citrate—1 mM disodium salt of EDTA.

Digestion of the thus obtained phage DNA was carried out as follows. Three units of HindIII were added to 1 μg of the DNA and the reaction was carried out at 37° C. for 3 hours in 20 μl of a buffer containing 10 mM Tris-HCl (pH 7.6), 7 mM MgCl₂, 7 mM β-mercaptoethanol and 50 mM NaCl. At the completion of the reaction 1 μl of 250 mM disodium salt of EDTA (pH 8.0) was added to the reaction mixture.

(B) Cleavage of Plasmid pBR322 DNA

One unit of HindIII was added to 1 μg of pBR322 DNA and the reaction was carried out at 37° C. for 3 hours in 20 μl of the same buffer as used for the digestion of the phage DNA. At the completion of the reaction 1 μl of 250 mM disodium salt of EDTA (pH 8.0) was added to the reaction mixture.

(C) Ligation

Five μl of 1.5 M sodium acetate (pH 7.0) was added to 20 μl of each of the restriction enzyme-treated DNA solutions prepared in (A) and (B) above, respectively. Each mixture was supplemented with 75 μl of ethanol, allowed to stand at −70° C. for 10 minutes and subjected to centrifugation at 12,000 rpm for 5 minutes. Each precipitate was collected, washed again with ethanol, then dried under reduced pressure and dissolved in 10 μl of 10 mM Tris-HCl (pH 8.0) - 1 mM disodium salt of EDTA (hereinafter referred to as TE buffer).

Ligation was carried out, either at 4° C. for 48 hours or at 20° C. for several hours, in 20 μl of a mixture containing 50 ng of the digested pBR322 DNA which was obtained in (B), 1.5 μg of the cleaved SφC DNA which was obtained in (A), 30 mM Tris-HCl (pH 7.6), 10 mM MgCl₂, 10 mM dithiothreitol, 0.1 mM ATP and 0.1 unit of T4 ligase. One μl of 250 mM disodium salt of EDTA (pH 8.0) was added to the reaction mixture to terminate the reaction. The reaction mixture was heated at 65° C. for 5 minutes to inactivate the ligase and stored at −20° C. after addition of 180 μl of TE buffer.

(D) Introduction of Recombinant Plasmid into *E. coli*

Each *E. coli* strain was inoculated into 10 ml of L-broth (pH 7.0) consisting of 1% polypeptone, 0.5% yeast extract and 0.5% NaCl and grown to 5×10⁸ cells/ml. The mixture was centrifuged at 4° C. to collect the cells. The cells were suspended in 5 ml of chilled 50 mM CaCl₂ and allowed to stand for 5 minutes in an ice-water bath. The suspension was then centrifuged again to collect the cells. The cells are suspended in 0.67 ml of chilled 50 mM CaCl₂ and the suspension was allowed to stand for 5 minutes in an ice-water bath. The *E. coli* suspension was mixed with 0.33 ml of a solution of the ligated plasmid DNA prepared in (C) above and the mixture was kept for 5 minutes in an ice-water bath. The reaction mixture was held at 42° C. for 2 minutes to terminate introduction of the recombinant plasmid into *E. coli*. The resulting suspension was, either as such or after being diluted ten or one hundred fold, plated on a L-broth agar medium containing 40 μg ampicillin per ml. The medium was incubated overnight at 37° C. to grow the *E. coli* transformants which had gained resistance to ampicillin.

(E) Selective Separation of SAK Producing *E. coli*

Five ml each of human plasma was charged into test tubes and heated at 56° C. for 20 minutes. Separately, ten ml each of liquefied 2% agar-containing nutrient agar medium was charged into test tubes and kept warm at 56° C. These two preparations were promptly mixed together in petri dishes and allowed to stand until the mixture was solidified. Aliquots of sample suspensions of the *E. coli* cells obtained in (D) above were spotted on the thus prepared agar medium and incubated at 37° C. There were observed colonies around which transparent fibrinolytic halos appeared. The halos indicated that the microbes of the colonies have SAK production capability.

The *E. coli* strains forming such colonies are the novel *E. coli* according to the present invention. One of the obtained novel strains is designated as *E. coli* K12 C600 $r_K^-m_K^-$ (pSAK 361) and another one as *E. coli* K12 WA802 $r_K^-m_K^=$ (pSAK 361), corresponding to the host *E. coli* strain, respectively.

(F) Analysis of *E. coli* Plasmid

The thus obtained *E. coli* cells of each strain were grown at 37° C. in 400 ml of L-broth containing 40 μg ampicillin per ml to about $4 \times 10^8$ cells/ml. At this point the culture was supplemented with chloramphenicol in a manner such that the latter's concentration became 150 μg/ml, and then subjected to further cultivation at 37° C. for 15 hours followed by centrifugation to collect the cells. The cells were washed in 50 ml of 10 mM Tris-HCl (pH 8.0)—0.015 M NaCl—1.5 mM sodium citrate and then suspended in 3.2 ml of 25% sucrose—50 mM Tris-HCl (pH 8.0). The suspension was supplemented with 1.6 ml of 250 mM disodium salt of EDTA (pH 8.0), 1 ml of 5 mg/ml lysozyme and 6 ml of 2% Brij-58 (KAO-ATLAS Co., Ltd.)—62.5 mM disodium salt of EDTA—50 mM Tris-HCl (pH 8.0) and incubated at 30° C. for 15 minutes to lyse mildly the cell walls. The mixture was subjected to high speed (30,000 rpm) centrifugation at 4° C. for 30 minutes to precipitate the cells. The supernatant was subjected to CsCl-ethidium bromide equilibrium density gradient centrifugation (36,000 rpm) at 10° C. for 48 hours to purify the plasmid DNA. The resulting plasmid DNA was digested with HindIII in accordance with the same procedure as described in (B) above. The length of the SAK gene-carrying DNA was determined to be 4.9 kb upon measurement by agarose gel electrophoresis using 1% agarose.

(G) Separation of 4.9 kb Fragment

One hundred μg of SφC DNA was digested by reacting the same, at 37° C. for 20 hours, with a mixture containing 10 mM Tris-HCl (pH 7.6), 7 mM MgCl₂, 7 mM β-mercaptoethanol, 50 mM NaCl and 100 units HindIII. The reaction mixture was subjected to agarose gel electrophoresis using 1% agarose. DNA was stained with ethidium bromide and only the desired region of the gel, i.e., the region containing the 4.9 kb DNA fragment was cut out. The 4.9 kb DNA fragment was eluted from an agarose gel electrophoretically into a dialysis tubing. The DNA eluate was treated with TE buffer saturated phenol and the aqueous phase was treated first with ether and then with ethanol to precipitate DNA. The resulting DNA is ready for use in ligation with vector DNAs.

(H) Production, Extraction and Purification of SAK

The SAK producing *E. coli* cells obtained above were inoculated into 50 ml of L-broth containing 0.1% glucose, and subjected, overnight at 37° C., to cultivation with shaking. The resulting culture was inoculated into 5 liters of the same broth as used above, and subjected to shaking culture at 37° C. for 12 hours. The culture was then centrifuged to collect cells. The cells were suspended in 200 ml of 100 mM Tris-HCl (pH 8.0)— 20% sucrose and the suspension was centrifuged again to collect cells. The cells were resuspended in 45 ml of 100 mM Tris-HCl (pH 8.0) - 20% sucrose and the suspension was supplemented with 5 ml of a lysozyme solution (5 mg/ml lysozyme in 20 mM disodium salt of EDTA, pH 8.0) and then allowed to stand in an ice-water bath for 1 hour. The mixture was centrifuged to collect the supernatant. To the supernatant was added ammonium sulfate to 80% saturation. The mixture was allowed to stand overnight at 4° C. and then centrifuged to collect the precipitate. The precipitate was dissolved in 10 ml of 10 mM Tris-HCl (pH 7.5) and dialyzed against the same buffer. The dialysate was subjected to Sephadex G-75 gel chromatography and eluted with 10 mM Tris-HCl (pH 7.5) to collect fractions of SAK activity. The fractions so collected were adsorbed to a column of CM-cellulose equilibrated with 10 mM Tris-HCl (pH 7.5), and subjected to linear gradient elution with 0–0.5 M NaCl. Fractions of SAK activity were collected which were eluted with 0.3–0.32 M NaCl.

EXAMPLE II

In this example, SφC was used as the DNA donor, HindIII and PstI as the restriction enzymes for digesting SφC DNA, pBR322 as the vector EcoRI and PstI as the restriction enzymes for digesting pBR322 DNA, and *E. coli* K12 C600 $r_K^-m_K^-$ and *E. coli* K12 WA802 $r_K^-m_K^=$ as the *E. coli* host.

(A) Digestion of Phage SφC DNA

Following the procedures described in Example I A through F, 4.9 kb fragment obtained by digesting the SφC DNA with HindIII was isolated. The single-stranded portions, present at both termini of the fragment and each consisting of four bases, were modified into double-strands by reacting the fragment at 18° C. for 4 hours with 1 unit of T4 DNA polymerase and four kinds of deoxyribonucleoside triphosphates - thymidine triphosphate, deoxyadenosine triphosphate, deoxyguanosine triphosphate and deoxycytidine triphosphate; (25 μM each) in 20 μl of a buffer containing 67 mM Tris-HCl (pH 8.0), 6.7 mM MgCl$_2$ and 6.7 mM β-mercaptoethanol. To the reaction mixture were added 5 μl of 1.5 M sodium acetate (pH 7.0) and 75 μl of ethanol. The mixture was held at −70° C. for 10 minutes and then subjected to centrifugation at 12,000 rpm for 5 minutes. The precipitate was washed with ethanol and dissolved in a buffer containing 10 mM Tris-HCl (pH 7.6) -7 mM MgCl$_2$—7 mM β-mercaptoethanol—50 mM NaCl. To the solution was added 0.5 unit of PstI and the reaction was carried out at 37° C. for 3 hours to further digest the fragment into two segments, which were ready for use in ligation in (C) below.

(B) Cleavage of Plasmid pBR322 DNA

One unit of BcoRI was added to 1 μg of pBR322 DNA and the reaction was carried out in the same manner as in Example I (B) to effect the cleavage. The single-stranded portions, present at both termini of the cleaved DNA and consisting of four bases, were modified into double strands in the same manner as in (A) above using T4 DNA polymerase and four kinds of deoxyribonucleoside triphosphates - thymidine triphosphate, deoxyadenosine triphosphate, deoxyguanosine triphosphate and deoxycytidine triphosphate. The resulting entirely double-stranded DNA was digested with PstI in the same manner as in (A) above. The digests were ready for use in ligation in (C) below.

(C) Ligation

The DNA fragments from SφC DNA and plasmid pBR322 DNA were mixed together and subjected to ligation in the same manner as in Example I (C), except that the amount of T4 DNA ligase used was 1 unit. (D) Subsequently, the same procedures as in Example 1 were followed to obtain two novel E. coli strains, which were designated E. coli K12 C600 $r_K{}^-m_K{}^-$ (pSAK-HP2) and E. coli K12 WA802 $r_K{}^-m_K{}^=$ (pSAK-HP2). Plasmid analysis revealed that the DNA of each of the E. coli strains had SφC-derived genetic information for SAK production of about 2.5 kb, in terms of DNA length, inserted.

EXAMPLE III

In this example, Pφ1 was used as the DNA donor, pBR322 as the vector, HindIII as the restriction enzyme and E. coli K12 C600 $r_K{}^-m_K{}^-$ as the E. coli host. (A) Preparation, and digestion with HindIII, of phage Pφ1 DNA, as well as Digestion of vector DNA, were carried out in the same manner as in Example I. (B) Ligation, introduction into E. coli, and selection of recombinant E. coli cells were carried out in the same manner as in Example I. (C) As a result of these operations, the DNA segment carrying genetic information for SAK production, which segment was derived from Pφ1, was successfully introduced into the E. coli strain. The resulting novel E. coli strain was designated as E. coli K12 C600 $r_K{}^-m_K{}^-$ (pSAK 601).

Cultures of the following microorganisms which may be prepared in accordance with the present invention were deposited at the American Type Culture Collection, Rockville, MD 20852 on the indicated dates.

| Deposit Date | Scientific Description | Depositors Reference | ATCC Designation |
|---|---|---|---|
| 8/18/82 | Escherichia coli | WA802 $r_K{}^-m_K{}^+$ (pSAK 361) | 39178 |
| 8/18/82 | Escherichia coli | C600 $r_K{}^-m_K{}^-$ (pSAK-HP2) | 39179 |

The culture designated as ATCC 39178 is described hereinabove in Example I step (E). The culture designated as ATCC 39179 is described hereinabove in Example II step (D).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A coliform bacillus having a periplasmic space, comprising: a recombinant DNA carrying genetic information capable of producing staphylokinase which accumulates in high concentrations in the periplasmic space of said coliform bacillus, said genetic information being DNA derived from a temperate phage DNA of Staphylococcus aureus.

2. The coliform bacillus of claim 1, which is Escherichia coli.

3. The Escherichia coil of claim 2, which is devoid of restriction capability.

4. Escherichia coli which comprises a recombinant DNA carrying genetic information for the production of staphylokinase, said genetic information being DNA derived from a temperate phage DNA of Staphylococcus aureous.

5. The Escherichia coli of claim 4, wherein said Escherichia coli is devoid of restriction capability.

6. The Escherichia coli of claim 4, which is identified by ATCC No. 39178.

7. The Escherichia coli of claim 4, which is identified by ATCC No. 19179.

8. The Escherichia coli of claim 4, wherein Escherichia coli K12 C600 is the Escherichia coli.

9. The Escherichia coli of claim 4, wherein Escherichia coli K12 WA802 is the Escherichia coli.

10. The Escherichia coli of claim 4, wherein said recombinant DNA comprises a vector DNA selected from the group consisting of ColE1, pMB9, pSC101, p15A and derivatives thereof and Charon vectors derived from λ phage; and a phage DNA fragment carrying genetic information for the production of staphylokinase derived from a phage strain selected from the group consisting of 42D, L42E, 77, Pφ1, Pφ2, Tφ-42D, Pφ-406, Rφ19 and SφC, said vector DNA and said phage DNA fragment being connected in such a manner that the capability of said vector for replication is not impaired.

11. The Escherichia coli of claim 4, wherein said recombinant DNA is prepared by digesting phage SφC with HindIII restriction enzyme to obtain a SφC phage DNA digest, digesting pBR322 DNA with HindIII restriction enzyme to obtain a pBR322 plasmid digest and ligating phage digest with said plasmid digest to obtain a recombinant plasmid.

12. The Escherichia coli of claim 4, wherein said recombinant DNA is prepared by further treating said recombinant DNA with HindIII restriction enzyme, digesting the resulting DNA with PstI restriction enzyme to form a fragment of DNA containing the gene for staphylokinase production and a fragment of DNA which does not contain the gene for staphylokinase production, cleaving pBR322 DNA with BcoRI to form a pBR322 digest, ligating said fragment of DNA which contains the gene for staphylokinase production with said pBR322 digest to obtain a plasmid of pBR322 having S$\phi$C-derived genetic information for staphylokinase production.

13. The *Escherichia coli* of claim 4, wherein said recombinant DNA is prepared by digesting phage P$\phi$1 with HindIII restriction enzyme to obtain a P$\phi$1 phage DNA digest, digesting pBR322 DNA with HindIII restriction enzyme to obtain a pBR322 plasmid digest and ligating said phage digest and said plasmid digest to obtain a recombinant plasmid.

14. The *Escherichia coli* of claim 4, wherein said genetic information for the production of staphylokinase is derived from S$\phi$C.

15. The *Escherichia coli* of claim 4, wherein the phage DNA fragment carrying genetic information for the production of staphylokinase is derived from P$\phi$1.

16. A recombinant DNA capable of imparting staphylokinase producing capability to a coliform bacillus, comprising: a vector DNA; and a phage DNA fragment derived from a temperate phage DNA of *Staphylococcus aureus* carrying genetic information for the production of staphylokinase, said vector DNA and said phage DNA fragment being connected in such a manner that the capability of said vector for replication is not impaired.

17. The recombinant DNA of claim 16, wherein said vector DNA is a plasmid.

18. The recombinant DNA of claim 16, wherein said vector DNA is an *Escherichia coli* plasmid.

19. The recombinant DNA of claim 16, wherein said vector DNA is a Charon vector derived from λ phage.

20. The recombinant DNA of claim 16, which comprises a vector DNA selected from the group consisting of ColE1, pMB9, pSC101, p15A and derivatives thereof and Charon vectors derived from λ phage; and a phage DNA fragment carrying genetic information for the production of staphylokinase derived from a phage strain selected from the group consisting of 42D, L42E, 77, P$\phi$1, P$\phi$2, T$\phi$-42D, P$\phi$-406, R$\phi$19 and S$\phi$C.

21. The recombinant DNA of claim 16, which is prepared by digesting phage S$\phi$C with HindIII restriction enzyme to obtain a S$\phi$C phage DNA digest, digesting pBR322 with HindIII restriction enzyme to obtain a pBR322 plasmid digest and ligating said phage digest with said plasmid digest to obtain a recombinant plasmid.

22. A recombinant DNA which is prepared by treating the recombinant DNA of claim 21 with HindIII restriction enzyme, digesting the resulting DNA with PstI restriction enzyme to form a fragment of DNA containing the gene for staphylokinase production and a fragment of DNA which does not contain the gene for staphylokinase production, cleaving pBR322 DNA with BcoRI to form a pBR322 digest, ligating said fragment of DNA which contains the gene for staphylokinase production with said pBR322 digest to obtain a plasmid of pBR322 having S$\phi$C-derived genetic information for staphylokinase production.

23. The recombinant DNA of claim 16, which is prepared by digesting phage P$\phi$1 with HindIII restriction enzyme to obtain a P$\phi$1 phage DNA digest, digesting pBR322 DNA with HindIII restriction enzyme to obtain pBR322 plasmid digest and ligating said phage digest and said plasmid digest to obtain a recombinant plasmid.

24. The recombinant DNA of claim 16, wherein the phage DNA fragment carrying genetic information for the production of staphylokinase is derived from S$\phi$C.

25. The recombinant DNA of claim 16, wherein the phage DNA fragment carrying genetic information for the production of staphylokinase is derived from P$\phi$1.

26. A process for the production of staphylokinase, comprising the steps of: culturing a coliform bacillus comprising a recombinant DNA carrying genetic information capable of producing staphylokinase which accumulates in high concentrations in the periplasmic space of said coliform bacillus, said genetic information being DNA derived from a temperate phage DNA of *Staphylococcus aureus* until a recoverable quantity of staphylokinase is produced; and collecting the thus produced staphylokinase.

27. The process of claim 26, wherein staphylokinase which has accumulated in cultured *Escherichia coli* cells is collected.

28. The process of claim 27, which comprises harvesting the cultured *Escherichia coli* cells and selectively collecting staphylokinase from the periplasmic fraction of said cells.

29. The process of claim 27, wherein said *Escherichia coli* is identified by ATCC No. 39178.

30. The process of claim 27, wherein said *Escherichia coli* is identified by ATCC No. 39179.

31. A method for obtaining a coliform bacillus capable of producing staphylokinase, comprising the steps of:
 (a) digesting a temperate phage DNA of *Staphylococcus aureus* as a DNA donor with one or more restriction enzymes to obtain donor DNA fragments;
 (b) cleaving a vector DNA with one or more restriction enzymes;
 (c) inserting the fragment obtained in step (a) into the cleaved site of the vector DNA obtained in step (b) to obtain recombinant DNA;
 (d) introducing the thus obtained recombinant DNA into a coliform bacillus host; and
 (e) selectively separating transformed coliform bacillus cells which possess the capability of producing staphylokinase.

32. The method of claim 31, wherein said temperate phage DNA is digested with HindIII restriction enzyme and said vector DNA is cleaved with HindIII restriction enzyme.

33. The method of claim 31, wherein said coliform bacillus is *Escherichia coli*.

* * * * *